United States Patent
Zhang et al.

(10) Patent No.: US 9,346,042 B2
(45) Date of Patent: May 24, 2016

(54) PROCESS FOR REGENERATION OF IONIC LIQUID CATALYST

(71) Applicants: SHELL OIL COMPANY, Houston, TX (US); CHINA UNIVERSITY OF PETROLEUM, Beijing (CN)

(72) Inventors: Rui Zhang, Beijing (CN); Zhichang Liu, Beijing (CN); Chunming Xu, Beijing (CN); Xianghai Meng, Beijing (CN); Peter Anton August Klusener, Amsterdam (NL)

(73) Assignee: Shell Oil Company, Houston, TX (US)

( * ) Notice: Subject to any disclaimer, the term of this patent is extended or adjusted under 35 U.S.C. 154(b) by 39 days.

(21) Appl. No.: 14/369,215

(22) PCT Filed: Dec. 28, 2012

(86) PCT No.: PCT/EP2012/077082
§ 371 (c)(1),
(2) Date: Jun. 27, 2014

(87) PCT Pub. No.: WO2013/098407
PCT Pub. Date: Jul. 4, 2013

(65) Prior Publication Data
US 2015/0231624 A1    Aug. 20, 2015

(30) Foreign Application Priority Data
Dec. 30, 2011    (WO) ................ PCT/CN2011/084965

(51) Int. Cl.
*B01J 38/64* (2006.01)
*B01J 31/40* (2006.01)
*B01J 31/02* (2006.01)
*B01J 38/66* (2006.01)

(52) U.S. Cl.
CPC .......... *B01J 31/4069* (2013.01); *B01J 31/0279* (2013.01); *B01J 38/66* (2013.01); *B01J 2231/44* (2013.01)

(58) Field of Classification Search
CPC .................................. B01J 38/64; B01J 38/66
USPC .............................................. 502/25, 26, 514
See application file for complete search history.

(56) References Cited

U.S. PATENT DOCUMENTS

| | | | |
|---|---|---|---|
| 7,285,698 B2 | 10/2007 | Liu et al. | |
| 7,732,363 B2 | 6/2010 | Elomari et al. | |
| 7,732,364 B2 | 6/2010 | Chang et al. | |
| 7,956,002 B2 | 6/2011 | Elomari et al. | |
| 2007/0142211 A1 | 6/2007 | Elomari et al. | |
| 2007/0142213 A1 | 6/2007 | Elomari et al. | |
| 2007/0142214 A1 | 6/2007 | Elomari et al. | |
| 2007/0142215 A1 | 6/2007 | Harris et al. | |
| 2007/0142217 A1 | 6/2007 | Elomari et al. | |
| 2007/0142218 A1 | 6/2007 | Harris et al. | |
| 2007/0249485 A1 | 10/2007 | Elomari et al. | |
| 2007/0249486 A1 | 10/2007 | Elomari et al. | |
| 2009/0170687 A1 | 7/2009 | Luo et al. | |
| 2009/0170688 A1 | 7/2009 | Chang et al. | |
| 2009/0253572 A1 | 10/2009 | Elomari et al. | |
| 2010/0130804 A1 | 5/2010 | Timken et al. | |
| 2010/0197483 A1 | 8/2010 | Elomari et al. | |

FOREIGN PATENT DOCUMENTS

| | | |
|---|---|---|
| CN | 1184284 | 7/2003 |
| CN | 101360563 | 2/2009 |
| CN | 101619010 | 1/2010 |
| FR | 862059 | 2/1941 |
| WO | 2011015639 | 8/2010 |
| WO | 2011015636 | 2/2011 |
| WO | 2011015640 | 2/2011 |

OTHER PUBLICATIONS

Albright, L.F.; Present & Future Alkylation Processes in Refineries, 2009 American Chemical Society, Ind. Eng. Res, vol. 48, No. 3, pp. 1409-1413.

Corma, Avelino, et al.; Chemistry, Catalysts, and Processes for Isoparaffin-Olefin Alkylations Actual Situation & Future Trends, Catalysis Reviews: Science & Engineering, vol. 35(4), pp. 483-570, 1993.

Liu, Zhichang, et al.; Ionic Liquid Alkylation Process Produces High-Quality Gasoline, Processing, Oil & Gas Jrnl., vol. 104, No. 40, pp. 52-56, Oct. 23, 2006.

*Primary Examiner* — Edward Johnson

(57) ABSTRACT

The present invention relates to a regeneration process for producing a regenerated ionic liquid catalyst from solids formed in an ionic liquid alkylation process wherein a first ionic liquid is used as a catalyst which is a composite ionic liquid comprising ammonium cations, and anions being composite coordinate anions derived from two or more metal salts, the regeneration process comprising (a) removing the solids from the reaction zone of the alkylation process; and (b) subsequently treating the solids with a second ionic liquid made from an ammonium salt as cation, and an aluminum salt as anion which is the same as the aluminum salt present in the first ionic liquid.

10 Claims, No Drawings

PROCESS FOR REGENERATION OF IONIC LIQUID CATALYST

PRIORITY CLAIM

The present application is the National Stage (§371) of International Application No. PCT/EP2012/077082, filed Dec. 28, 2012, which claims priority from International Application No. PCT/CN2011/084965, filed Dec. 30, 2011, the disclosures of which are incorporated herein by reference.

FIELD OF THE INVENTION

The present invention provides a process for regeneration of an ionic liquid catalyst.

BACKGROUND OF THE INVENTION

There is an increasing demand for alkylate fuel blending feedstock. As a fuel-blending component alkylate combines a low vapour pressure, no sulfur, olefins or aromatics with high octane properties. The most desirable components in the alkylate are trimethylpentanes (TMPs), which have research octane numbers (RONs) of greater than 100. Such an alkylate component may be produced by reacting isobutane with a butene in the presence of a suitable acidic catalyst, e.g. HF or sulfuric acid, although other catalysts such a solid acid catalyst have been reported. Recently, the alkylation of isoparaffins with olefins using an acidic ionic liquid catalyst has been proposed as an alternative to HF and sulfuric acid catalysed alkylation processes.

For instance, U.S. Pat. No. 7,285,698 discloses a process for manufacturing an alkylate oil, which uses a composite ionic liquid catalyst to react isobutane with a butene. In the process of U.S. Pat. No. 7,285,698, isobutane and a butene are supplied to a reactor and the alkylate is formed by contacting the reactants with a composite ionic liquid under alkylation conditions. The reactor effluent is separated and the ionic liquid phase is recycled to the reactor while the hydrocarbon phase is treated to retrieve the alkylate. It has however been found that during operation of an ionic liquid alkylation process, solids are formed. As the reaction progresses, these solids accumulate in the reaction zone and may lead to blockage of pathways and/or valves. In WO2011/015639 a process is described for removal of the solids formed during the ionic liquid alkylation process. According to that process, the solids are completely removed and disposed of. This is economically unfavourable and very undesirable from an environmental point of view. Therefore, there is a need for (at least partial) regeneration of the solids formed in the ionic liquid alkylation process.

SUMMARY OF THE INVENTION

It has been found that the solids that are formed during the operation of an ionic liquid alkylation process wherein a composite ionic liquid is used as the catalyst (see e.g. WO2011/015639), may be regenerated into a composite ionic liquid.

Accordingly, the present invention provides a regeneration process for producing a regenerated ionic liquid catalyst from solids formed in an ionic liquid alkylation process wherein a first ionic liquid is used as a catalyst which is a composite ionic liquid comprising ammonium cations, and anions being composite coordinate anions derived from two or more metal salts, wherein at least one metal salt is an aluminium salt and any further metal salt is a salt of a metal selected from the group consisting of Group IB elements of the Periodic Table, Group IIB elements of the Periodic Table and transition elements of the Periodic Table, the regeneration process comprising
(a) removing the solids from the reaction zone of the alkylation process; and
(b) subsequently treating the solids with a second ionic liquid made from an ammonium salt as cation, and an aluminium salt as anion which is the same as the aluminium salt present in the first ionic liquid.

By removing at least part of the solids formed during the alkylation reaction, the accumulation of solids in the reaction zone is prevented. Thus, the process is not contaminated nor hindered by solids. Furthermore, by regeneration of the solids to produce regenerated catalyst and re-use that catalyst in the alkylation process the environmental impact and costs of the process can be reduced.

DETAILED DESCRIPTION OF THE INVENTION

The solids that are used in the regeneration process according to the invention are formed in a process wherein an alkylate is prepared by reacting an isoparaffin with an olefin, in particular isobutane and a butene. The obtained alkylate is particularly suitable for gasoline blending purposes or for use in aviation gasoline production. In the alkylation process, the isoparaffin and the olefin are provided to a reaction zone. In the reaction zone a hydrocarbon mixture comprising isoparaffin and olefin is contacted with a catalyst suitable for alkylation. The hydrocarbon mixture comprises olefin typically supplied externally, i.e. fresh olefin, and comprises isoparaffin. The isoparaffin may be externally supplied isoparaffin, i.e. fresh isoparaffin, and/or isoparaffin which is recycled from any other part of the process. The (fresh) isoparaffin and olefin may be supplied to the process separately, however typically the (fresh) isoparaffin and the (fresh) olefin are provided to the reaction zone as a mixture comprising isoparaffin and olefin.

In the present alkylation process the catalyst is a composite mixture comprising the ionic liquid (herein below also referred to a catalyst). Ionic liquids are known in the art for their ability to catalyse alkylation reactions. The catalyst used in the present alkylation process is a composite ionic liquid comprising cations derived from a hydrohalide of an alkyl-containing amine, imidazolium or pyridine. Preferably, the cations comprise cations of ammonium salts, for example nitrogen atoms, which are saturated with four substituents, among which there is at least one hydrogen atom and one alkyl group. More preferably, the alkyl substituent is at least one selected from methyl, ethyl, propyl, butyl, amyl, and hexyl groups. Examples of preferred ammonium cations include triethylammonium (NEt$_3$H$^+$) and methyldiethylammonium cations (MeNEt$_2$H$^+$), cations in which the nitrogen is part of a cyclic structure (e.g. like in piperidine and pyrrolidine) or

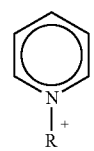

The anions of the composite ionic liquid are preferably derived from aluminium based Lewis acids, in particular aluminium halides, preferably aluminium (III) chloride. Due the high acidity of the aluminium chloride Lewis acid it is preferred to combine the aluminium chloride, or other aluminium halide, with a second or more metal halide, sulfate or nitrate to form a coordinate anion, in particular a coordinate anion derived from two or more metal halides, wherein at least one metal halide is an aluminium halide. Suitable further metal halides, sulfates or nitrates, may be selected from halides, sulfates or nitrates of metals selected from the group consisting of Group IB elements of the Periodic Table, Group IIB elements of the Periodic Table and transition elements of the Periodic Table. Preferred metals include copper, iron, zinc, nickel, cobalt, molybdenum, silver or platinum. Preferably, the metal halides, sulfates or nitrates, are metal halides, more preferably chlorides or bromides, such as copper (I) chloride, copper (II) chloride, nickel (II) chloride, iron (II) chloride. Preferably, the molar ratio of the aluminium compound to the other metal compounds in the range of from 1:100-100:1, more preferably of from 1:1-100:1, or even more preferably of from 2:1-30:1. By using a coordinate anion comprising aluminium and another metal, an improved alkylate product may be obtained. A method for preparing such catalyst is for instance described in U.S. Pat. No. 7,285,698. Particularly preferred catalysts are acidic ionic liquid catalysts comprising a coordinate anion derived from aluminium(III) chloride and copper(II) chloride or aluminium(III) chloride and copper(I) chloride.

As mentioned herein above, the hydrocarbon mixture comprising isoparaffin and olefin is contacted with the catalyst in the reaction zone. The hydrocarbon mixture is mixed in the reaction zone with the catalyst to form a reaction mixture. As the reaction progresses the reaction mixture will, besides hydrocarbon reactants and acidic ionic liquid, additionally comprise products. Mixing of the hydrocarbon mixture and the catalyst may be done by any suitable means for mixing two or more liquids, including dynamic and static mixers. In contact with the catalyst, the isoparaffins and olefins react under alkylation conditions to form an alkylate.

The formed alkylate is obtained from the reaction zone in the form of an alkylate-comprising effluent. The alkylate-comprising effluent still comprises a substantial amount of unreacted isoparaffin. Therefore, part of the alkylate-comprising effluent may be recycled to the reaction zone to maintain a high ratio of isoparaffin to olefin in hydrocarbon mixture in the reaction zone.

At least part of the alkylate-comprising effluent of the reaction zone is separated in a separator unit into a hydrocarbon-rich phase and an ionic liquid catalyst-rich phase. At least part of the hydrocarbon-rich phase is treated and/or fractionated (e.g. by distillation) to retrieve the alkylate and optionally other components in the hydrocarbon phase, such as unreacted isoparaffin or n-paraffins. Preferably, such isoparaffin is at least partly reused to form part of the isoparaffin feed provided to the process. This may be done by recycling at least part of the isoparaffin, or a stream comprising isoparaffin obtained from the fractionation of the hydrocarbon-rich phase, and combining it with the isoparaffin feed to the process.

Reference herein to a hydrocarbon-rich phase is to a phase comprising more than 50 mol % of hydrocarbons, based on the total moles of hydrocarbon and ionic liquid catalyst.

Reference herein to an ionic liquid catalyst-rich phase is to a phase comprising more than 50 mol % of ionic liquid catalyst, based on the total moles of hydrocarbon and ionic liquid catalyst.

Due to the low affinity of the ionic liquid for hydrocarbons and the difference in density between the hydrocarbons and the ionic liquid catalyst, the separation between the two phases is suitably done using for example well known settler means, wherein the hydrocarbons and catalyst separate into an upper predominantly hydrocarbon phase and lower predominantly catalyst phase or by using any other suitable liquid/liquid separator. Such liquid/liquid separators are known to the skilled person and include cyclone and centrifugal separators. The catalyst phase is generally recycled back to the reactor.

As described herein before, during the alkylation reaction solids are formed in the reaction zone. Reference herein to solids is to non-dissolved solid particles. The solids predominantly consist out of metals, metal compounds and/or metal salts which were originally comprised in the composite ionic liquid catalyst. Preferably, the solids comprise at least 10 wt % metal, i.e. either in metallic, covalently bound or ionic form, based the total weight of the solids, wherein the metal is a metal that was introduced to the process as part of the acidic ionic liquid catalyst. The solids may also comprise contaminant components, which were introduced into the reaction mixture as contaminants in the hydrocarbon mixture or the composite ionic liquid. Alternatively, the solids may be the product of a chemical reaction involving any of the above-mentioned compounds.

The solids may have any size, however the solids typically have an average size of in the range of from 0.1 to 10 µm. In particular, at least 50% of the solids have a particle size below 5 µm, more particular 80% of the solids have a particle size below 5 µm based on the total number of solid particles.

In WO2011015639 it is described that although during mixing these solids are dispersed throughout the reaction mixture, upon separation of the alkylate-comprising effluent it was found that the solids, to a large extent, accumulate in the composite ionic liquid catalyst-rich phase. If the catalyst-rich phase is subsequently recycled to the reaction zone to become part of the reaction mixture in the reaction zone, the solids accumulate in the reaction zone, resulting in undesirably high solids content in the reaction zone. A high solids content in the reaction zone may for instance result in blockage of pathways or valves in the reactor zone and pipes to and from the separation unit, due to precipitation of solids. In addition, at high solids content the solids may agglomerate to form large aggregates, resulting in increased blockage risk. Therefore, (at least part of) the solids are removed from the reaction zone. It is not required to remove all solids from the reaction zone. Preferably, solids are removed from the reaction zone to an extent that the reaction mixture (i.e. a mixture comprising hydrocarbon reactants, composite ionic liquid and products) comprises in the range of from 0.05 to 5 wt %, more preferably at most 2 wt % of solids, based on the total weight composite ionic liquid in the reaction zone.

Although it is believed that part of the catalyst is lost when forming the solids, the catalyst alkylation performance is not significantly affected. Loss of catalyst due to solids formation merely means that a small fraction of the total catalyst inventory is inactivated or lost, while the remainder of the catalyst remains unaffected.

The solids may be removed from the reaction zone at any time or place in the process. It is possible to remove the solids from the reaction mixture directly inside the reaction zone. However, preferably, at least part of the reaction mixture is withdrawn from the reaction zone as a solids-comprising effluent. This solids-comprising effluent comprises next to the solid also hydrocarbons and composite ionic liquid, wherein the hydrocarbons typically include isoparaffins and alkylate. Subsequently, (at least part of) the solids in at least part of the solids-comprising effluent are removed. After the removal of solids a solids-depleted effluent is obtained. Preferably, at least part of the solids-depleted effluent is recycled to the reactor for efficient use of the materials.

The solids from the solids-comprising effluent withdrawn from the reaction (as described herein before) may be removed immediately after withdrawal of the solids-comprising effluent from the reaction zone. However, preferably, the solids-comprising effluent is first separated in a typical separator unit into a catalyst-rich phase and a hydrocarbon-rich phase and the solids are subsequently removed from the catalyst-rich phase. Subsequently, the solids-depleted catalyst can be reintroduced into the reaction zone.

The solids may be removed by any suitable means for removing solids from liquids, including but not limited to filtration, precipitation (e.g. in a settler unit) and centrifugation processes, and processes using a cyclone. Such processes are well known in the art. Thus, according to the present invention, in step (a) at least part of the reaction mixture of the alkylation process is withdrawn from the reaction zone as a solids-comprising effluent, followed by separation of the effluent in a separator unit into a catalyst-rich phase and a hydrocarbon-rich phase and the solids are subsequently removed from the catalyst-rich phase by appropriate means. In view of process efficiency, centrifugation is the preferred process for removing the solids from the catalyst-rich phase.

Due to the specific nature of ionic liquids it is preferred that the removal of the solids is performed at such a temperature that the acidic ionic liquid catalyst is liquid. In particular, it is preferred to remove the solids at a temperature in the range of from 5 to 80° C., more preferably of from 20 to 60° C., while ensuring that the temperature is such that the ionic liquid remains a liquid. By removing the solids at elevated temperatures, the viscosity of the ionic liquid is lower while the density is reduced, which may be beneficial in view of decreased time and power input required to obtained separation of the solids from the liquid.

The solids may be removed from the process in any form, however typically the solids are removed in the form of a paste of solids. Such a paste may comprise next to solid particles for instance some residual ionic liquid and/or hydrocarbons (which may be for instance some polymeric material formed as side product during the reaction). Depending on the amount of residual ionic liquid, the solids may also be removed from the process in the form of a slurry. In this text, the term "paste" is meant to also refer to "slurry". Typically, a paste contains at least 30% of solid particles.

According to the process for regeneration of solids according to the present invention, in step (b) the solids are preferably treated in the form of a paste. Preferably, the cation in the second ionic liquid used in step (b) is the same as the cation present in the first ionic liquid as used in the alkylation process. In a further embodiment of the invention, the anion in the first ionic liquid is a composite coordinate anion derived from aluminium (III) chloride and copper (I) chloride. In a preferred embodiment of the invention, the anion in the second ionic liquid is derived from aluminium (III) chloride. In a further embodiment, the molar ratio of the aluminium salt to the ammonium salt in the second ionic liquid ranges from 1.3 to 2.2, preferably 1.6 to 2.0, and more preferred 1.6 to 1.8. In a preferred embodiment, the cation in the first ionic liquid and the cation in the second ionic liquid are derived from a triethylammonium salt, and preferably from triethylammonium chloride.

In another embodiment, the solids in step (b) are stirred for some time, preferably at least a few hours, e.g. about 4 hours, with the second ionic liquid at a temperature from 15 to 100° C., preferably from 20 to 80° C., most preferably from 25 to 45° C.

The residual solids remaining after stirring the solids with the second ionic liquid, are removed—preferably by centrifugation. The resulting ionic liquid is recycled to the reaction zone and reused in the alkylation process. Thus, a further embodiment of the present invention relates to an ionic liquid alkylation process comprising a regeneration process as described herein, wherein after the regeneration process (at least part of) the regenerated ionic liquid catalyst is recycled to the reaction zone of the alkylation process.

Some further process details of the alkylation process are described below.

In the alkylation process, an isoparaffin and an olefin are reacted to form an alkylate by contacting the hydrocarbon mixture comprising isoparaffin and olefin with the catalyst under alkylation conditions. Preferably, the hydrocarbon mixture comprises at least isobutane and optionally isopentane, or a mixture thereof, as an isoparaffin. The hydrocarbon mixture preferably comprises at least an olefin comprising in the range of from 2 to 8 carbon atoms, more preferably of from 3 to 6 carbon atoms, even more preferably 4 or 5 carbon atoms. Examples of suitable olefins include, propene, 1-butene, 2-butene, isobutene, 1-pentene, 2-pentene, 2-methyl-1-butene, 3-methyl-1-butene, 2-methyl-2-butene.

Isoparaffins and olefins are supplied to the process in a molar ratio, which is preferably 1 or higher, and typically in the range of from 1:1 to 40:1, more preferably 1:1 to 20:1. In the case of a continuous process, excess isoparaffin can be recycled for reuse in the hydrocarbon mixture.

The alkylation conditions (or process conditions) are those known in the art for this type of alkylation processes. Actual operational process conditions are for example dependent of the exact composition of the hydrocarbon mixture and catalyst, and the like.

The temperature in the alkylation reactor is preferably in the range of from −20 to 100° C., more preferably in the range of from 0 to 50° C. In any case the temperature must be high enough to ensure that the ionic liquid catalyst is in the liquid state.

To suppress vapour formation in the reactor, the process may be performed under pressure; preferably the pressure in the reactor is in the range of from 0.1 to 1.6 MPa.

Preferably, the composite ionic liquid catalyst to hydrocarbon ratio in the alkylation reaction zone is at least 0.5, preferably 0.9 more preferably at least 1. Preferably, the composite ionic liquid catalyst to hydrocarbon ratio in the reaction zone is in the range of from 1 to 10.

The hydrocarbon mixture may be contacted with the catalyst in any suitable alkylation reactor. The hydrocarbon mixture may be contacted with the catalyst in a batch-wise, a semi-continuous or continuous process. Reactors such as used in liquid acid catalysed alkylation can be used (see L. F. Albright, Ind. Eng. Res. 48 (2009) 1409 and A. Corma and A. Martinez, Catal. Rev. 35 (1993) 483); alternatively the reactor is a loop reactor, optionally with multiple injection points for the hydrocarbon feed, optionally equipped with static mixers to ensure good contact between the hydrocarbon mixture and catalyst, optionally with cooling in between the injection points, optionally by applying cooling via partial vaporization of volatile hydrocarbon components (see Catal. Rev. 35 (1993) 483), optionally with an outlet outside the reaction zone (see WO2011/015636). In the prior art diagrams are available of alkylation process line-ups which are suitable for application in the process of this invention, e.g. in U.S. Pat. No. 7,285,698, Oil & Gas J., vol 104 (40) (2006) p 52-56 and Catal. Rev. 35 (1993) 483.

EXAMPLES

The invention is illustrated by the following non-limiting examples.

Example 1

Isobutane and butene (C4 feed) were fed in a 1:1 molar ratio in ca. 2 kg/h during 5.5 days to a continuous alkylation unit (e.g. as described in Oil & Gas J., vol 104 (40) (2006) p 52-56; FIG. 3 therein) in which 30 kg of composite ionic liquid derived from triethylammonium chloride, aluminium (III) chloride and copper(I) chloride (produced by China University of Petroleum Beijing) was circulated. The C4 feed was mixed with isobutane which was recycled from the fractionator whereby the molar ratio isobutane/butene (I/O ratio) was varied between 6-10. The resulting mixture was mixed with the hydrocarbon phase recycled from the top of the settler to achieve on average an I/O ratio of ca. 100. The resulting hydrocarbon mixture was fed into the reactor, equipped with a static mixer, together with an equal volumetric flow of ionic liquid recycled from the bottom of the settler. The temperature of the reactor was kept between 10-30° C. The reactor outlet was connected to the middle of the settler. The ionic liquid was collected in the bottom and recycled to the reactor and the hydrocarbon phase in the top was split into a recycle to the hydrocarbon feed to the reactor and to a product stream to the fractionator. In the fractionator the alkylate was collected in the bottom and isobutane was distilled off and recycled to the C4 feed. The alkylate was removed from the bottom of the fractionator from time to time. At the end of the run the ionic liquid was collected and filtered. The filter cake was washed with the isobutane inventory of the alkylation unit. The paste collected from the filter is called sample 1#.

Example 2

The method as of example 1 was repeated, however with the following differences. The I/O ratio in the mixture of the C4 feed and the isobutane recycle was 5. The reactor temperature was 35° C. The run time was ca. 2.5 days. Instead of filtration, the ionic liquid (IL) was passed two times at a rate of 50 kg/h through a tubular centrifuge rotating at ca. 20000 rounds per minute. The paste collected from the centrifuge is called sample 2#.

Example 3

The method as of example 2 was repeated, however with the following differences. The I/O ratio in the mixture of the C4 feed and the isobutane recycle was 10. The reactor temperature was 40° C. The run time was ca. 2 days. The paste collected from the centrifuge is called sample 3#.

Example 4

The method as of example 2 was repeated, however with the following differences. The I/O ratio in the mixture of the C4 feed and the isobutane recycle was 10. The run time was ca. 2 days. The paste collected from the centrifuge is called sample 4#.

Example 5

From ionic liquid used in the commercial trial as described in Oil&Gas J., vol 104 (40) (2006) p 52-56, which was stored at room temperature in air tight drums, were taken two samples: paste from the bottom and liquid from the top. Both samples were combined and heated to 35° C., and subsequently centrifuged in a laboratory centrifuge at 4500 r/min for 2 h. The liquid fraction was removed. The remaining paste is called sample 5#.

Example 6

(a) Dissolving Capacity in Basis Ionic Liquid 100 g of paste sample 1# was mixed with 100 mL of basis ionic liquid $Et_3NHCl$-$1.6AlCl_3$. The mixture was stirred at 25° C. for 4 hours. The resulting mixture was centrifuged at 4500 rpm for 2 hours. The liquid phase was removed and the paste (residue) was weighed: 68.68 g.

The dissolving capacity is defined as: (100 g-68.68 g residue)/100 mL=31.32 g/100 mL.

(b) Alkylation Properties of Regenerated Ionic Liquid 100 mL of the liquid phase from example 6(a) was placed in a 500 mL bench scale autoclave unit (see C. P. Huang et al. Applied Catalysis A: General 277 (2004) 41-43; FIG. 1 therein). A C4 feed composed as listed in Table 1 was fed to the autoclave at a rate of 700 mL/h.

TABLE 1

| Components of mixture C4 feed (used in examples 6-13) | |
|---|---|
| component | content, wt % |
| propane | 0.86 |
| 1-butene | 0.54 |
| t-2-butene | 2.09 |
| c-2-butene | 2.01 |
| iso-butene | 0.05 |
| n-butane | 2.51 |
| iso-butane | 91.9 |
| C6+ | 0.04 |

Reaction temperature and stir speed were kept 15° C. and 1300 r/min respectively. When the autoclave had completely filled with liquid a sample was taken and the hydrocarbon phase was analyzed by gas chromatography. The distribution of the alkylate fraction (in terms of C5-7, octanes: trimethylpentanes (TMPs) and dimethylhexanes (DMHs), and C9+) and the weight average research octane number (RON) was calculated from the individual weight fractions of the hydrocarbon components. The results are listed in Table 2.

Examples 7-8

In two separate experiments, example 6 was repeated at 80 and 150° C., for dissolving paste sample 1# with 100 mL of basis ionic liquid. The results are listed in Table 2.

Examples 9-11

In three separate experiments, example 6 was repeated at 25, 80 and 150° C. for dissolving paste sample 1# with 100 mL of basis ionic liquid, in these cases being $Et_3NHCl$-$1.8AlCl_3$. The results are listed in Table 2.

Comparative Example 12

100 mL of the basis ionic liquid $Et_3NHCl$-$1.6AlCl_3$ was placed in a 500 mL bench scale autoclave unit. A C4 feed composed as listed in Table 1 was fed to the autoclave at a rate of 700 mL/h. Reaction temperature and stir speed were kept 15° C. and 1300 r/min respectively. When the autoclave had completely filled with liquid a sample was taken and the hydrocarbon phase was analyzed by gas chromatography. The distribution of the alkylate fraction and the RON was calculated from the individual weight fractions of the hydrocarbon components. The results are listed in Table 2.

Comparative Example 13

Example 12 was repeated, however with fresh composite IL instead of basis ionic liquid $Et_3NHCl$-$1.6AlCl_3$. The results are listed in Table 2.

TABLE 2

Results examples 6-13

| | | dissolving capacity results | | alkylation properties obtained with remaining liquid phase | | | | | |
|---|---|---|---|---|---|---|---|---|---|
| | | dissolving temperature | dissolving capacity | distribution of alkylate, wt % | | | | | |
| example | basis ionic liquid | °C. | g/100 mL | C5-C7 | TMP | DMH | C9+ | TMP/DMH | RON |
| 6 | Et$_3$NHCl-1.6AlCl$_3$ | 25 | 31.32 | 7.60 | 78.68 | 5.22 | 8.49 | 15.07 | 93.77 |
| 7 | Et$_3$NHCl-1.6AlCl$_3$ | 80 | 19.26 | 8.81 | 77.06 | 5.60 | 8.53 | 13.77 | 93.35 |
| 8 | Et$_3$NHCl-1.6AlCl$_3$ | 150 | 7.91 | 6.95 | 74.92 | 6.03 | 12.01 | 12.42 | 90.62 |
| 9 | Et$_3$NHCl-1.8AlCl$_3$ | 25 | 27.67 | 6.73 | 80.12 | 5.01 | 8.14 | 15.99 | 95.09 |
| 10 | Et$_3$NHCl-1.8AlCl$_3$ | 80 | 24.47 | 6.48 | 79.59 | 5.58 | 8.35 | 14.26 | 93.75 |
| 11 | Et$_3$NHCl-1.8AlCl$_3$ | 150 | 8.65 | 7.20 | 75.25 | 6.48 | 10.08 | 11.61 | 90.46 |
| comparative example | comparative ionic liquids | | | alkylation properties obtained with comparative ionic liquids | | | | | |
| 12 | Et$_3$NHCl-1.6AlCl$_3$ | | | 25.82 | 35.91 | 16.40 | 21.87 | 2.19 | 70.83 |
| 13 | fresh composite IL | | | 5.83 | 79.52 | 5.79 | 8.86 | 13.73 | 93.62 |

Comparison of examples 6-11 with examples 12 and 13 shows that by dissolving the paste in the basis ionic liquid, the remaining liquid phase shows increased TMP/DMH ratio and RON selectivity, which is comparable to that of fresh composite ionic liquid.

Example 14

(a) Dissolving Capacity in Basis Ionic Liquid 100 g of paste sample 2# was mixed with 100 mL of basis ionic liquid Et$_3$NHCl-1.6AlCl$_3$. The mixture was stirred at 45° C. for 4 hours. The resulting mixture was centrifuged at 4500 rpm for 2 hours. The liquid phase was removed and the paste (residue) was weighed: 39.43 g.

The dissolving capacity is defined as: (100 g-39.43 g residue)/100 mL=60.57 g/100 mL.

(b) Alkylation Properties of Regenerated Ionic Liquid 100 mL of the liquid phase from example 14(a) was placed in a 500 mL bench scale autoclave unit. A C4 feed composed as listed in Table 2 was fed to the autoclave at a rate of 700 mL/h.

TABLE 3

Components of mixture C4 feed (used in examples 14-17)

| component | content w % |
|---|---|
| propane | 0.35 |
| t-2-butene | 2.3 |
| c-2-butene | 2.27 |
| n-butane | 7.5 |
| iso-butane | 87.57 |

Reaction temperature and stir speed were kept 15° C. and 1300 r/min respectively. When the autoclave had completely filled with liquid a sample was taken and the hydrocarbon phase was analyzed by gas chromatography. The distribution of the alkylate fraction and the RON was calculated from the individual weight fractions of the hydrocarbon components. The results are listed in Table 4.

Examples 15 and 16

In two separate experiments, example 14 was repeated with the paste samples 3# and 4# as indicated in Table 4.

Comparative Example 17

An experiment similar to example 13 was performed, the difference being that the feed as listed in Table 3 was used. The results are listed in Table 4.

TABLE 4

Results examples 14-17

| | | | dissolving capacity results | alkylation properties obtained with remaining liquid phase | | | | | |
|---|---|---|---|---|---|---|---|---|---|
| | | | dissolving capacity | distribution of alkylate, wt % | | | | | |
| example | basis ionic liquid | paste sample | g/100 mL | C5-C7 | TMP | DMH | C9+ | TMP/DMH | RON |
| 14 | Et$_3$NHCl-1.6AlCl$_3$ | 2# | 60.57 | 1.59 | 91.28 | 4.68 | 2.45 | 19.49 | 99.72 |
| 15 | Et$_3$NHCl-1.6AlCl$_3$ | 3# | 48.35 | 2.72 | 86.25 | 7.08 | 3.95 | 12.18 | 97.05 |
| 16 | Et$_3$NHCl-1.6AlCl$_3$ | 4# | 47.95 | 3.94 | 85.51 | 6.98 | 3.57 | 12.25 | 97.66 |
| comparative example | comparative ionic liquid | | | alkylation properties obtained with comparative ionic liquid | | | | | |
| 17 (comp) | fresh composite IL | | | 3.58 | 87.03 | 6.55 | 2.84 | 13.29 | 98.39 |

Comparison of examples 14-16 with example 17 shows that by dissolving the paste in the basis ionic liquid, the remaining liquid phase shows a TMP/DMH ratio and RON selectivity comparable to that of fresh composite ionic liquid.

Example 18

(a) Dissolving Capacity in Basis Ionic Liquid 100 g of paste sample 5# was mixed with 100 mL of basis ionic liquid $Et_3NHCl$-$1.6AlCl_3$. The mixture was stirred at 25° C. for 4 hours. The resulting mixture was centrifuged at 4500 rpm for 2 hours. The liquid phase was removed and the paste (residue) was weighed: 16.77 g.

The dissolving capacity is defined as: (100 g-16.77 g residue)/100 mL=83.23 g/100 mL.

Examples 19-22

In four separate experiments, example 18 was repeated at different dissolving temperatures and/or with different basis ionic liquids as indicated in Table 6.

Comparative Example 23

Experiment 12 was repeated, the difference being that basis ionic liquid $Et_3NHCl$-$1.8AlCl_3$ and feed as listed in Table 5 were used. The results are listed in Table 6.

Comparative Example 24

Experiment 13 was repeated, the difference being that feed as listed in Table 5 was used. The results are listed in Table 6.

TABLE 6

Results examples 18-24

| | dissolving capacity results | | | alkylation properties obtained with | | | | | |
|---|---|---|---|---|---|---|---|---|---|
| | | dissolving | | remaining liquid phase | | | | | |
| | | temperature | capacity | distribution of alkylate, w % | | | | | |
| example | basis ionic liquid | ° C. | g/100 mL | C5-C7 | TMP | DMH | C9+ | TMP/DMH | RON |
| 18 | $Et_3NHCl$-$1.6AlCl_3$ | 25 | 83.23 | 8.92 | 76.12 | 5.56 | 9.40 | 13.69 | 92.70 |
| 19 | $Et_3NHCl$-$1.8AlCl_3$ | 25 | 79.08 | 7.17 | 79.13 | 5.39 | 8.31 | 14.68 | 94.19 |
| 20 | $Et_3NHCl$-$1.8AlCl_3$ | 80 | 63.59 | 10.33 | 63.26 | 8.63 | 17.78 | 7.33 | 87.62 |
| 21 | $Et_3NHCl$-$1.8AlCl_3$ | 150 | 49.15 | 11.18 | 61.79 | 8.86 | 18.17 | 6.97 | 85.60 |
| 22 | $Et_3NHCl$-$2.0AlCl_3$ | 25 | 44.15 | 5.37 | 83.65 | 5.57 | 5.41 | 15.01 | 95.29 |
| comparative example | comparative ionic liquid | | | alkylation properties obtained with comparative ionic liquid | | | | | |
| 23 (comp) | $Et_3NHCl$-$1.8AlCl_3$ | | | 20.53 | 39.86 | 15.91 | 23.71 | 2.51 | 73.65 |
| 24 (comp) | fresh composite IL | | | 5.02 | 84.29 | 5.30 | 5.39 | 15.90 | 95.81 |

(b) Alkylation Properties of Regenerated Ionic Liquid 100 mL of the liquid phase from example 18(a) was placed in a 500 mL bench scale autoclave unit. A C4 feed composed as listed in Table 5 was fed to the autoclave at a rate of 700 mL/h.

TABLE 5

Components of mixture C4 feed (used in examples 18-24)

| component | content w % |
|---|---|
| propane | 0.23 |
| 1-butene | 0.29 |
| t-2-butene | 2.65 |
| c-2-butene | 1.71 |
| iso-butene | 0.08 |
| n-butane | 1.95 |
| iso-butane | 93.02 |
| C6+ | 0.07 |

Reaction temperature and stir speed were kept 15° C. and 1300 r/min respectively. When the autoclave had completely filled with liquid a sample was taken and the hydrocarbon phase was analyzed by gas chromatography. The distribution of the alkylate fraction and the RON was calculated from the individual weight fractions of the hydrocarbon components. The results are listed in Table 6.

Comparison of examples 18-22 with examples 23 and 24 shows that by dissolving the paste in the basis ionic liquid, the remaining liquid phase shows increased TMP/DMH ratio and RON selectivity, which is comparable to that of fresh composite ionic liquid.

That which is claimed is:

1. A regeneration process for producing a regenerated ionic liquid catalyst from solids formed in an ionic liquid alkylation process wherein a first ionic liquid is used as a catalyst which is a composite ionic liquid comprising ammonium cations, and anions being composite coordinate anions derived from two or more metal salts, wherein at least one metal salt is an aluminium salt and any further metal salt is a salt of a metal selected from the group consisting of Group IB elements of the Periodic Table, Group IIB elements of the Periodic Table and transition elements of the Periodic Table, the regeneration process comprising
    (a) removing the solids from the reaction zone of the alkylation process; and
    (b) subsequently treating the solids with a second ionic liquid made from an ammonium salt as cation, and an aluminium salt as anion which is the same as the aluminium salt present in the first ionic liquid.

2. The process of claim 1, wherein in step (a) at least part of the reaction mixture of the alkylation process is withdrawn from the reaction zone as a solids-comprising effluent, followed by separation of the effluent in a separator unit into a catalyst-rich phase and a hydrocarbon-rich phase and the solids are subsequently removed from the catalyst-rich phase by filtration, precipitation or centrifugation.

3. The process of claim 1, wherein the solids treated in step (b) are in the form of a paste.

4. The process of claim 1, wherein the cation in the second ionic liquid is the same as the cation present in the first ionic liquid.

5. The process of claim 1, wherein the anion in the first ionic liquid is a composite coordinate anion derived from aluminium (III) chloride and copper (I) chloride.

6. The process of claim 1, wherein the anion in the second ionic liquid is derived from aluminium (III) chloride.

7. The process of claim 1, wherein the molar ratio of the aluminium salt to the ammonium salt in the second ionic liquid ranges from 1.3 to 2.2.

8. The process of claim 1, wherein the cation in the first ionic liquid and the cation in the second ionic liquid are derived from a triethylammonium salt.

9. The process of claim 1, wherein the solids in step (b) are stirred with the second ionic liquid at a temperature from 15 to 100° C.

10. An ionic liquid alkylation process comprising a regeneration process according to claim 1, wherein after the regeneration process (at least part of) the regenerated ionic liquid catalyst is recycled to the reaction zone of the alkylation process.

* * * * *